United States Patent
Deur-Bert et al.

(10) Patent No.: US 11,198,663 B2
(45) Date of Patent: Dec. 14, 2021

(54) METHOD FOR STORING 1,1,1,2,3,3-HEXAFLUOROPROPANE AND CONTAINER FOR STORING SAME

(71) Applicant: Arkema France, Colombes (FR)

(72) Inventors: Dominique Deur-Bert, Charly (FR); Laurent Wendlinger, Soucieu en Jarrest (FR)

(73) Assignee: Arkema France, Colombes (FR)

( * ) Notice: Subject to any disclaimer, the term of this patent is extended or adjusted under 35 U.S.C. 154(b) by 7 days.

(21) Appl. No.: 16/625,811

(22) PCT Filed: Jul. 16, 2018

(86) PCT No.: PCT/FR2018/051796
§ 371 (c)(1),
(2) Date: Dec. 23, 2019

(87) PCT Pub. No.: WO2019/016457
PCT Pub. Date: Jan. 24, 2019

(65) Prior Publication Data
US 2021/0156518 A1    May 27, 2021

(30) Foreign Application Priority Data

Jul. 17, 2017 (FR) .................................. 1756727

(51) Int. Cl.
| | | |
|---|---|---|
| *C07C 19/08* | (2006.01) | |
| *C07C 17/38* | (2006.01) | |
| *B65D 90/02* | (2019.01) | |
| *F17C 1/14* | (2006.01) | |
| *F17C 13/00* | (2006.01) | |

(52) U.S. Cl.
CPC .............. *C07C 17/38* (2013.01); *B65D 90/02* (2013.01); *F17C 1/14* (2013.01); *F17C 13/002* (2013.01); *C07C 19/08* (2013.01); *F17C 2203/0604* (2013.01); *F17C 2203/0607* (2013.01); *F17C 2203/0641* (2013.01); *F17C 2203/0643* (2013.01); *F17C 2203/0646* (2013.01); *F17C 2203/0648* (2013.01)

(58) Field of Classification Search
CPC ................................ C07C 17/42; C07C 19/08
See application file for complete search history.

(56) References Cited

U.S. PATENT DOCUMENTS

| | | | |
|---|---|---|---|
| 1,858,022 A * | 5/1932 | Martin | C07C 17/42 |
| | | | 570/121 |
| 4,442,246 A | 4/1984 | Brown | |
| 5,396,000 A | 3/1995 | Nappa et al. | |
| 5,679,875 A | 10/1997 | Aoyama et al. | |
| 8,359,964 B2 | 1/2013 | Pfersmann | |
| 8,389,779 B2 | 3/2013 | Avril et al. | |
| 2012/0021247 A1* | 1/2012 | Komatsu | F25B 49/005 |
| | | | 428/646 |
| 2015/0051426 A1* | 2/2015 | Fukushima | F17C 1/00 |
| | | | 570/136 |
| 2016/0289148 A1 | 10/2016 | Masato | |

OTHER PUBLICATIONS

Epa ("New Chemical Alternative for Ozonedepleting Substances: HFC-236EA" Oct. 2, 2008, pp. 1-2) (Year: 2008).*
ISA/EP; International Search Report and Written Opinion for International Patent Application No. PCT/FR2018/051796 dated Dec. 21, 2018, 14 pages.
AHRI Standard 700, "2011 Standards for Specifications for Fluorocarbon Refrigerants", AHRI: Air-Conditioning Heating and Refrigeration Institute, AHRI Standard 700-2011, Jan. 1, 2001, 19 pages, XP003035362.

\* cited by examiner

*Primary Examiner* — Medhanit W Bahta
(74) *Attorney, Agent, or Firm* — NK Patent Law

(57) ABSTRACT

The present invention relates to a method for storing, in a closed container, a composition comprising 1,1,1,2,3,3-hexafluoropropane in a liquid/gas state composed of a liquid phase and of a gas phase, characterized in that i) a stream comprising 1,1,1,2,3,3-hexafluoropropane is injected into said container, said stream comprising an oxygen concentration of at most 5000 ppm by volume at a temperature of 25° C., and ii) the container is closed after injection of said stream. The present invention also relates to a container for storing 1,1,1,2,3,3-hexafluoropropane.

10 Claims, No Drawings

METHOD FOR STORING 1,1,1,2,3,3-HEXAFLUOROPROPANE AND CONTAINER FOR STORING SAME

CROSS-REFERENCE TO RELATED APPLICATIONS

This application is a U.S. National Stage application of International Patent Application No. PCT/FR2018/051796, filed on Jul. 16, 2018, which claims the benefit of French Patent Application No. 1756727, filed on Jul. 17, 2017.

TECHNICAL FIELD

The present invention relates to a method for storing a compound of fluoropropane type. In particular, the present invention relates to a method for storing 1,1,1,2,3,3-hexafluoropropane. The present invention also relates to a container for storing a compound of fluoropropane type, in particular 1,1,1,2,3,3-hexafluoropropane.

TECHNOLOGICAL BACKGROUND OF THE INVENTION 1,1,1,2,3,3-Hexafluoropropane (HFC-236ea) is, for example, capable of being used as a cleaning agent in the semiconductor industry. 1,1,1,2,3,3-Hexafluoropropane (HFC-236ea) is a hydrofluorocarbon and has been described as a starting material for the manufacture of 1,1,1,2,3-pentafluoropropene or as an intermediate in the manufacture of 1,1,1,2,3-pentafluoropropane and/or of 1,1,1,2-tetrafluoropropene. Mention may in particular be made of the documents U.S. Pat. Nos. 5,679,875, 539,600, 8,359,964 and 8,389,779.

HFC-236ea is stored and transported in a closed pressurized container at ambient temperature. The HFC-236ea thus transported in the closed container is in a liquid/gas state composed of a liquid phase and of a gas phase. In addition, HFC-236ea in a liquid/gas state has to be stable over the entire duration of its storage in order to maintain a quality suitable for its subsequent use. During this duration of storage, the formation of impurities has to be minimized.

SUMMARY OF THE INVENTION

The present invention is targeted at providing a method for stable storage of 1,1,1,2,3,3-hexafluoropropane.

According to a first aspect, the present invention relates to a method for storing, in a closed container, a composition comprising 1,1,1,2,3,3-hexafluoropropane in a liquid/gas state composed of a liquid phase and of a gas phase, characterized in that i) a stream comprising 1,1,1,2,3,3-hexafluoropropane is injected into said container, said stream comprising an oxygen concentration of at most 5000 ppm by volume at a temperature of 25° C., and ii) the container is closed after injection of said stream.

According to a preferred embodiment, the oxygen concentration is at most 100 ppm by volume at a temperature of 25° C.

According to a preferred embodiment, after closing the container, the content by weight in said liquid phase of compound A comprising a group of formula (I) is less than 5000 ppm, based on the total weight of said liquid phase; —[—C(CX$_3$)(X)—C(X)$_2$]$_n$— (I), with each X independently selected from the group consisting of H and F, and n being an integer of between 2 and 100.

According to a second aspect, the present invention relates to a container for storing 1,1,1,2,3,3-hexafluoropropane containing a composition comprising 1,1,1,2,3,3-hexafluoropropane in a liquid/gas state composed of a liquid phase and of a gas phase, said composition comprising an oxygen concentration in said gas phase of at most 5000 ppm by volume at a temperature of 25° C.

According to a preferred embodiment, the oxygen concentration in said gas phase is at most 100 ppm by volume at a temperature of 25° C.

According to a preferred embodiment, the content by weight in said liquid phase of compound A comprising a group of formula (I) is less than 5000 ppm, based on the total weight of said liquid phase; —[—C(CX$_3$)(X)—C(X)$_2$]$_n$— (I), with each X independently selected from the group consisting of H and F, and n being an integer of between 2 and 100.

According to a preferred embodiment, the container withstands a test pressure, said test pressure being of between 10 and 100 bar, advantageously between 15 and 70 bar, preferably between 20 and 60 bar, in particular from 40 to 50 bar.

According to a preferred embodiment, the container is made of a material selected from carbon steel, stainless steel, manganese steel, chromium/molybdenum steel or an aluminum alloy.

According to a preferred embodiment, the container comprises an internal surface in contact with said composition, said internal surface being at least partially covered with a coating comprising zinc or with a resin of polyether or polyol type.

According to a preferred embodiment, said composition comprises at least 98% by weight of 1,1,1,2,3,3-hexafluoropropane, based on the total weight of the composition.

DETAILED DESCRIPTION OF THE INVENTION

According to a first aspect of the present invention, a method for storing a composition comprising 1,1,1,2,3,3-hexafluoropropane is provided. Said composition comprising 1,1,1,2,3,3-hexafluoropropane is in a liquid/gas state, that is to say composed of a liquid phase and of a gas phase. The present method makes it possible to store said composition in a closed container. Preferably, said container comprises at least one valve for filling or emptying said container.

Preferably, the present method comprises a stage during which a stream comprising 1,1,1,2,3,3-hexafluoropropane is injected into said container. Preferably, said stream comprises an oxygen concentration of at most 5000 ppm by volume at a temperature of 25° C.

Preferably, the oxygen concentration is at most 4000 ppm by volume at a temperature of 25° C., more preferentially at most 3000 ppm by volume, in particular at most 2000 ppm by volume, more particularly at most 1000 ppm by volume, favorably at most 500 ppm, advantageously favorably at most 250 ppm, preferentially favorably at most 100 ppm, more preferentially favorably at most 50 ppm, particularly favorably at most 10 ppm, by volume, at a temperature of 25° C.

According to a preferred embodiment, after closing the container, the content by weight in said liquid phase of compound A comprising a group of formula —[—C(CX$_3$)(X)—C(X)$_2$]$_n$— (I) is less than 5000 ppm, based on the total weight of said liquid phase, with each X independently selected from the group consisting of H and F, and n being an integer of between 2 and 100. Preferably, the content by weight of compound A in said liquid phase is determined by withdrawing a sample of said condensed composition at a temperature of 5° C.

Advantageously, the content by weight in said liquid phase of compound A comprising a group of formula (I) is less than 4000 ppm, preferably less than 3000 ppm, more preferentially less than 2000 ppm, in particular less than 1000 ppm, more particularly less than 800 ppm, favorably less than 600 ppm, more favorably less than 400 ppm, preferentially favorably less than 200 ppm, particularly favorably less than 100 ppm, based on the total weight of said liquid phase. The limitation of compound A to the contents indicated above according to the present invention makes it possible to maintain a high degree of purity of the 1,1,1,2,3,3-hexafluoropropane composition even after several days of storage. This represents a very particular advantage for the subsequent uses of the 1,1,1,2,3,3-hexafluoropropane.

Preferably, the compound A comprises a group of formula (Ia), (Ib), (Ic), (Id), (Ie), (If) and/or (Ig) as described below:

—[—C(CF$_3$)(F)—C(F)$_2$]$_n$— (Ia)

—[—C(CF$_3$)(F)—C(H)$_2$]$_n$— (Ib)

—[—C(CF$_3$)(H)—C(F)(H)]$_n$— (Ic)

—[—C(CF$_3$)(H)—C(H)$_2$]$_n$— (Id)

—[—C(CF$_3$)(H)—C(F)$_2$]$_n$— (Ie)

—[—C(CF$_3$)(F)—C(F)(H)]$_n$— (If)

—[—C(CHF$_2$)(F)—C(F)$_2$]$_n$— (Ig)

Preferably, the compound A comprises a group of formula (Ih): —[[C(CF$_3$)(F)—C(F)$_2$]$_n$]$_m$—[[C(CF$_3$)(F)—C(H)$_2$]$_n$]$_o$—[[C(CF$_3$)(H)—C(F)(H)]$_n$]$_p$—[[C(CF$_3$)(H)—C(H)$_2$]$_n$]$_q$—[[C(CF$_3$)(H)—C(F)$_2$]$_n$]$_r$—[[C(CF$_3$)(F)—C(F)(H)]$_n$]$_s$—[[C(CHF$_2$)(F)—C(F)$_2$]$_n$]$_t$— (Ih) with m, o, p, q, r, s and t independently being an integer from 0 to 100, provided that at least two among m, o, p, q, r, s and t are other than 0. Preferably, m, o, p, q, r, s and t are independently an integer from 0 to 80, more preferentially from 0 to 60, in particular from 0 to 40, more particularly from 0 to 20. In particular, m, o, p, q, r, s and t are independently 0, 1, 2, 3, 4, 5, 6, 7, 8, 9, 10, 11, 12, 13, 14, 15, 16, 17, 18, 19 or 20.

Preferably, n is a number between of between 2 and 80. More preferably, n is a number between of between 2 and 60. In particular, n is an integer between 2 and 40. More particularly, n is an integer between 5 and 20. Favorably, n is an integer between 5 and 10. Thus, n can be 2, 3, 4, 5, 6, 7, 8, 9, 10, 11, 12, 13, 14, 15, 16, 17, 18, 19 or 20.

Said composition can also comprise one or more polymerization inhibitors selected, for example, from the group consisting of p-methoxyphenol, t-amylphenol, limonene, d,l-limonene, quinones, hydroquinones, epoxides, amines and the mixtures of these; preferably, the polymerization inhibitor is p-methoxyphenol or t-amylphenol. Preferably, the content by weight of polymerization inhibitor is from 50 to 1000 ppm, in particular from 100 to 500 ppm, based on the total weight of the composition.

According to a preferred embodiment, said stream can comprise compounds of formula CX$_3$—CX=CX$_2$ (II) with X being independently selected from H or F. Preferably, the compound of formula (II) is of formula CF$_3$CF=CF$_2$, CF$_3$CF=CH$_2$, CF$_3$CH=CHF, CF$_3$CH=CH$_2$, CF$_3$CF=CHF, CF$_3$CH=CF$_2$ or CHF$_2$CF=CF$_2$.

According to a second aspect of the present invention, a container for storing 1,1,1,2,3,3-hexafluoropropane is provided. Said container contains 1,1,1,2,3,3-hexafluoropropane in a liquid/gas state composed of a liquid phase and of a gas phase. Preferably, the oxygen concentration in said gas phase is at most 5000 ppm by volume at a temperature of 25° C. The second aspect of the invention thus relates to a receptacle, i.e. the container, which comprises a 1,1,1,2,3,3-hexafluoropropane composition. The container is defined by its resistance to the test and/or the material from which it is formed, as is described in the present patent application. The container also comprises at least one valve for making possible the introduction and/or the removal of 1,1,1,2,3,3-hexafluoropropane from it.

Preferably, the oxygen concentration in said gas phase is at most 4000 ppm by volume at a temperature of 25° C., more preferentially at most 3000 ppm by volume, in particular at most 2000 ppm by volume, more particularly at most 1000 ppm by volume, favorably at most 500 ppm, advantageously favorably at most 250 ppm, preferentially favorably at most 100 ppm, more preferentially favorably at most 50 ppm, particularly favorably at most 10 ppm, by volume, at a temperature of 25° C.

According to a preferred embodiment, the content by weight in said liquid phase of compound A comprising a group of formula (I) is less than 5000 ppm, based on the total weight of said liquid phase;

—[—C(CX$_3$)(X)—C(X)$_2$]$_n$— (I), with each X independently selected from the group consisting of H and F, and n being an integer of between 2 and 100.

Advantageously, the content by weight in said liquid phase of compound A comprising a group of formula (I) is less than 4000 ppm, preferably less than 3000 ppm, more preferentially less than 2000 ppm, in particular less than 1000 ppm, more particularly less than 800 ppm, favorably less than 600 ppm, more favorably less than 400 ppm, preferentially favorably less than 200 ppm, particularly favorably less than 100 ppm, based on the total weight of said liquid phase. Preferably, the content by weight of compound A in said liquid phase is determined by withdrawing a sample of said condensed composition at said temperature of 5° C.

Preferably, the compound A comprises a group of formula (Ia), (Ib), (Ic), (Id), (Ie), (If) and/or (Ig) or (Ih) as described above.

According to a preferred embodiment, compounds of formula CX$_3$—CX=CX$_2$ (II), with X being independently selected from H or F, can be present in said container, that is to say in the gas phase or in the liquid phase or both. Preferably, the compound of formula (II) is of formula CF$_3$CF=CF$_2$, CF$_3$CF=CH$_2$, CF$_3$CH=CHF, CF$_3$CH=CH$_2$, CF$_3$CF=CHF, CF$_3$CH=CF$_2$ or CHF$_2$CF=CF$_2$.

According to a preferred embodiment, said container comprises a content by weight of solid residue of less than 300 ppm, said solid residue comprising at least one group of formula (Ia) to (Ig) or (Ih) as described above. Preferably, said content of solid residue is less than 200 ppm, more preferentially less than 100 ppm, in particular less than 50 ppm, with respect to the total weight of said composition contained in said container. The limitation of the solid residues to the contents indicated above makes it possible to ensure good use of said container, by preventing in particular obstruction of the valve or valves of said container.

According to a preferred embodiment, the container withstands a test pressure, said test pressure being of between 10 and 100 bar, advantageously between 15 and 70 bar, preferably between 20 and 60 bar, in particular from 40 to 50 bar.

According to a preferred embodiment, the container is made of a material selected from carbon steel, stainless steel, manganese steel, chromium/molybdenum steel or an aluminum alloy.

According to a preferred embodiment, the container comprises an internal surface in contact with said composition, said internal surface being at least partially covered with a coating comprising zinc or with a resin of polyether or polyol type.

The resin of polyether or polyol type can result from monomers comprising an oxirane or phenol functional group. Preferably, the resin of polyether or polyol type results from monomers comprising a siloxirane unit. In particular, the resin of polyether or polyol type results from monomers comprising a siloxirane unit of formula (III):

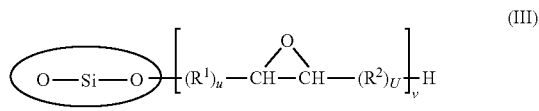

(III)

in which $R^1$ and $R^2$ are, independently of each other and independently for each unit n and m, a group of the following types: $C_6$-$C_{18}$ aryl, $C_1$-$C_{20}$ alkyl, $C_3$-$C_{20}$ cycloalkyl, $C_3$-$C_{20}$ cycloalkenyl, $C_2$-$C_{20}$ alkenyl, carbonyl of formula $R^3$—C(O)—$R^4$, ester of formula $R^3$—C(O)—O—$R^4$, ether of formula $R^3$—O—$R^4$; an amine of formula $R^3$—N—$R^4$, it also being possible for $R^2$ to be an aldehyde group of formula $R^3$—C(O)—H; $R^3$ and $R^4$ being chosen, independently of each other, from a $C_6$-$C_{18}$ aryl, $C_1$-$C_{20}$ alkyl, $C_3$-$C_{20}$ cycloalkyl, $C_3$-$C_{20}$ cycloalkenyl or $C_2$-$C_{20}$ alkenyl group;

v is an integer from 1 to 30, advantageously from 1 to 20, preferably from 5 to 10; and u is independently, for $R^1$ and $R^2$, an integer from 1 to 30, advantageously from 1 to 20, preferably from 5 to 10. According to another preferred embodiment, the resin of polyether or polyol type results from condensates of a compound A1 with a compound B1, the compound A1 being a substituted or unsubstituted phenol compound and the compound B1 being a compound of formula $R^1C(O)R^2$ in which $R^1$ and $R^2$ are independently hydrogen, $C_1$-$C_{20}$ alkyl, $C_6$-$C_{20}$ aryl, $C_3$-$C_{20}$ cycloalkyl or $C_2$-$C_{20}$ alkenyl. Preferably, the compound A1 is phenol $C_6H_5OH$ and the compound B1 is formaldehyde.

According to a preferred embodiment, at least 90% of said internal surface in contact with said composition is covered with said resin of polyether or polyol type, advantageously at least 95% of said internal surface in contact with said composition is covered with said resin of polyether or polyol type, preferably at least 98% of said internal surface in contact with said composition is covered with said resin of polyether or polyol type, in particular at least 99% of said internal surface in contact with said composition is covered with said resin of polyether or polyol type, more particularly the entire internal surface of the receptacle in contact with said composition is covered with said resin of polyether or polyol type.

The term "alkyl" denotes a monovalent radical resulting from a linear or branched alkane comprising from 1 to 20 carbon atoms. The term "cycloalkyl" denotes a monovalent radical resulting from a cycloalkane comprising from 3 to 20 carbon atoms. The term "aryl" denotes a monovalent radical resulting from an arene comprising from 6 to 18 carbon atoms. The term "alkenyl" denotes a monovalent radical of 2 to 20 carbon atoms and at least one carbon-carbon double bond. The term "halogen" refers to an —F, —Cl, —Br or —I group. The term "cycloalkenyl" refers to a monovalent radical resulting from a cycloalkene comprising from 3 to 20 carbon atoms. The $C_1$-$C_{20}$ alkyl, $C_2$-$C_{20}$ alkenyl, $C_2$-$C_{20}$ alkynyl, $C_3$-$C_{20}$ cycloalkyl, $C_3$-$C_{20}$ cycloalkenyl and $C_6$-$C_{18}$ aryl groups can be substituted or unsubstituted by one or more —OH, halogen, —NR$^a$C(O)R$^b$, —C(O)NR$^a$R$^b$, —NR$^a$R$^b$, —OR$^a$, —CO$_2$R$^a$, —OC(O)OR$^a$, —OC(O)R$^a$, —C(O)H or —C(O)R$^a$ substituents, in which R$^a$ and R$^b$ are, independently of each other, hydrogen, unsubstituted $C_1$-$C_{20}$ alkyl, unsubstituted $C_2$-$C_{20}$ alkenyl, unsubstituted $C_3$-$C_{20}$ cycloalkyl, unsubstituted $C_3$-$C_{20}$ cycloalkenyl or unsubstituted $C_6$-$C_{18}$ aryl. In the —NR$^a$R$^b$ substituents, R$^a$ and R$^b$ can form, with the nitrogen atom to which they are attached, a saturated or unsaturated, aromatic or non-aromatic, 5- to 10-membered heterocycle.

According to another preferred embodiment, the resin of polyether or polyol type results from condensates of a compound A1 with a compound B1, the compound A1 being a substituted or unsubstituted phenol compound and the compound B1 being a compound of formula $R^5C(O)R^6$ in which $R^5$ and $R^6$ are independently hydrogen, $C_1$-$C_{20}$ alkyl, $C_6$-$C_{20}$ aryl, $C_3$-$C_{20}$ cycloalkyl or $C_2$-$C_{20}$ alkenyl. The substituted phenol compound can be substituted by any one of the abovementioned substituents. Preferably, the compound A1 is an unsubstituted phenol. Advantageously, the compound B is a compound of formula $R^5C(O)R^6$ in which $R^5$ and $R^6$ are independently hydrogen, $C_1$-$C_{10}$ alkyl, $C_6$-$C_{10}$ aryl, $C_3$-$C_{10}$ cycloalkyl or $C_2$-$C_{10}$ alkenyl. Preferably, the compound B1 is a compound of formula $R^5C(O)R^6$ in which $R^5$ and $R^6$ are independently hydrogen, $C_1$-$C_5$ alkyl, $C_6$-$C_{10}$ aryl, $C_3$-$C_6$ cycloalkyl or $C_2$-$C_5$ alkenyl. In particular, the compound B1 is a compound of formula $R^5C(O)R^6$ in which $R^5$ and $R^6$ are hydrogen.

According to another preferred embodiment, at least 90% of said internal surface in contact with said composition can be covered with a coating comprising zinc, advantageously at least 95% of said internal surface in contact with said composition can be covered with a coating comprising zinc, preferably at least 98% of said internal surface in contact with said composition can be covered with a coating comprising zinc, in particular at least 99% of said internal surface in contact with said composition can be covered with a coating comprising zinc. More particularly, the entire internal surface in contact with said composition contained in said receptacle can be covered with a coating comprising zinc.

Preferably, the coating comprises at least 50% by weight of zinc, based on the total weight of the coating, advantageously at least 70% by weight, based on the total weight of the coating, preferably at least 90% by weight of zinc, based on the total weight of the coating, more preferentially at least 95% by weight of zinc, based on the total weight of the coating, in particular at least 99% of zinc, based on the total weight of the coating, more particularly at least 99.9% of zinc, based on the total weight of the coating.

Alternatively, the coating can be an alloy comprising zinc, preferably less than 50% by weight of zinc, based on the total weight of the coating. For example, the coating can be brass. Alternatively, the coating can comprise copper, advantageously at least 60% by weight of copper, based on the total weight of the coating, preferably at least 70% by weight of copper, based on the total weight of the coating, in particular at least 90% by weight of copper, based on the total weight of the coating. Alternatively, the receptacle as described in the present patent application can also have an internal surface, preferably the entire internal surface in contact with said composition, covered with a coating comprising copper or brass in place of zinc.

According to another preferred embodiment, said internal surface of said container is covered with a thermal insulator comprising a polymer material having closed pores, the latter being formed from and/or containing a haloalkene of formula (III) $R_2C=CRR'$ in which R is independently selected from the group consisting of Cl, F, H and $CF_3$ and R' is $(CR_2)_nY$, where Y is $CF_3$ and n is 0 or 1. Preferably, said haloalkene of formula (III) is selected from the group consisting of (E/Z)-1,1,1,4,4,4-hexafluoro-2-butene, (E/Z)-1-chloro-3,3,3-trifluoropropene and (Z/E)-1,3,3,3-tetrafluoropropene.

According to a preferred embodiment, said composition comprises at least 98% by weight of 1,1,1,2,3,3-hexafluoropropane, based on the total weight of the composition. Preferably, said composition comprises at least 99% by weight, in particular at least 99.4%, of 1,1,1,2,3,3-hexafluoropropane, based on the total weight of the composition.

Thus, the present invention provides, in this second aspect of the invention, an assemblage between a container as defined above and a composition comprising 1,1,1,2,3,3-hexafluoropropane, said composition being contained in said container.

EXAMPLES

A container made of carbon steel is filled with a composition comprising 98.2% by weight of 1,1,1,2,3,3-hexafluoropropane. A defined amount of oxygen is also introduced into the container. The latter is maintained at 60° C. for 14 days, the maximum temperature which can be reached during storage. The contents of the container are then discharged and condensed at a temperature of 5° C. The liquid phase and the gas phase are then analyzed. The results are shown in table 1 below.

|  | Oxygen concentration in the gas phase | Content of compound A in the liquid phase |
| --- | --- | --- |
| Ex. 1 | 50 ppm | <25 ppm |
| Ex. 2 | 2000 ppm | 813 ppm |
| Ex. 3 (comp.) | 6000 ppm | 6437 ppm |

The invention claimed is:

1. A method for storing, in a closed container, a composition composed of a liquid phase and a gas phase, the composition comprising 1,1,1,2,3,3-hexafluoropropane, the method comprising i. injecting a stream comprising 1,1,1,2,3,3-hexafluoropropane into said container, said stream comprising an oxygen concentration of at most 5000 ppm by volume at a temperature of 25° C., and ii. closing the container after injection of said stream.

2. The method as claimed in claim 1, wherein the oxygen concentration is at most 100 ppm by volume at a temperature of 25° C.

3. The method as claimed in claim 1, wherein, after closing the container, the liquid phase comprises compound A in a content by weight of less than 500 ppm, based on the total weight of said liquid phase; and wherein compound A comprises a group of formula (I), —[—C(CX$_3$)(X)—C(X)$_2$]$_n$— (I), with each X independently selected from the group consisting of H and F, and n being an integer of between 2 and 100.

4. A closed container for storing a composition composed of a liquid phase and a gas phase, the composition comprising 1,1,1,2,3,3-hexafluoropropane and oxygen, wherein an oxygen concentration in said gas phase is at most 5000 ppm by volume at a temperature of 25° C.

5. The container as claimed in claim 4, wherein the oxygen concentration in said gas phase is at most 100 ppm by volume at a temperature of 25° C.

6. The container as claimed in claim 4, wherein the liquid phase comprises compound A in a content by weight less than 5000 ppm, based on the total weight of said liquid phase; and wherein compound A comprises a group of formula (I), —[—C(CX$_3$)(X)—C(X)$_2$]$_n$— (I), with each X independently selected from the group consisting of H and F, and n being an integer of between 2 and 100.

7. The container as claimed in claim 4, wherein the container withstands a test pressure, said test pressure being of between 10 and 100 bar.

8. The container as claimed in claim 4, wherein the container is made of a material selected from the group consisting of carbon steel, stainless steel, manganese steel, chromium/molybdenum steel and an aluminum alloy.

9. The container as claimed in claim 4, wherein the container comprises an internal surface in contact with said composition, said internal surface being at least partially covered with a coating comprising zinc or with a resin of polyether or polyol.

10. The container as claimed in claim 4, wherein said composition comprises at least 98% by weight of 1,1,1,2,3,3-hexafluoropropane, based on the total weight of the composition.

* * * * *